United States Patent [19]

Nakano et al.

[11] Patent Number: 5,007,071

[45] Date of Patent: Apr. 9, 1991

[54] METHOD OF INSPECTING BONDED WAFERS

[75] Inventors: Masami Nakano; Takao Abe, both of Annaka, Japan

[73] Assignee: Shin-Etsu Handotai Co., Ltd., Tokyo, Japan

[21] Appl. No.: 421,756

[22] Filed: Oct. 16, 1989

[30] Foreign Application Priority Data

Oct. 14, 1988 [JP] Japan ................................ 63-260326

[51] Int. Cl.$^5$ .......................................... G01N 23/207
[52] U.S. Cl. ......................................... 378/74; 378/73
[58] Field of Search .............................. 378/70, 73, 74

[56] References Cited

U.S. PATENT DOCUMENTS

| | | | |
|---|---|---|---|
| 3,609,356 | 9/1971 | Schwuttke et al. | 378/74 |
| 3,944,823 | 3/1976 | Chikawa | 378/74 |
| 4,078,175 | 3/1978 | Fletcher et al. | 378/74 |

OTHER PUBLICATIONS

Takahiro Kojima et al., X-Ray Diffraction Microscopy by an Electronic Streak Camera System, Japanese Journal of Applied Physics, Jul. 1988, pp. 1331-1334.

B. Forque, Cartes A CMS, Les Rayons X au Secours du Test, mesures, Jun. 1988, pp. 33-34.

J. K. Wang et al., Nondestructive Diagnosis of Thick Production-Line Microelectronic Components Using Transmission Acoustic Microscope, Dec. 4-6, 1978, pp. 449-451.

"Real-Time X-Ray Topography: Defect Dynamics and Crystal Growth", by Queisser et al., *Journal of Crystal Growth* 52 (1981), 897-906.

"Application of X-Ray Topography to the Characterization of Semiconductor Surface Layers", by Wang et al., Conference: *Developments in Applied Spectroscopy*, Chicago, Ill., May 1968, pp. 31-60.

*Primary Examiner*—Craig E. Church
*Attorney, Agent, or Firm*—Cushman, Darby & Cushman

[57] ABSTRACT

A method of inspecting bonded wafers, which involves obtaining a Lang topograph of bonded wafers as a sample by using a Lang camera, or further treating an image thereon, thereby detecting unbonded regions at the interface of the bonded wafers. In bonding two silicon wafers to each other, an one-side surface of each silicon wafer is finished into a mirror surface and then is cleaned to a sufficient extent. Subsequently, both the mirror surfaces of the two silicon wafers are superposed one upon the other and then the superposed wafers are subjected to high-temperature heat treatment. The high-temperature heat treatment is conducted mainly for the purpose of removing distortions on the bonded surfaces, making the bonding interface monolithic, and, absorbing and diffusing a very small amount of atmospheric gas.

3 Claims, 6 Drawing Sheets

METHOD OF INSPECTING BONDED WAFERS

BACKGROUND OF THE INVENTION (Industrial Field of the Invention)

The present invention relates to a method of inspecting bonded wafers and especially relates to a method which is adapted to detect fine unbonded regions at the interface between the bonded wafers without fracture or destruction.

(Statement of the Related Art)

Thermal diffusion, epitaxial growth, and the like have hitherto been widely employed as technical methods of introducing impurities into a semiconductor material body in the manufacture of an electronic semiconductor device. Such prior art methods are employed because they have been well established from a technical point of view. However, when an attempt is made to produce a high power device by using one of the prior art methods, a technical limitation is imposed on the collector diffusion effected by thermal diffusion, or on the formation of a high-resistance layer of 100 Ωcm or more effected by epitaxial growth. This makes it difficult to provide a high power device of high voltage with large capacity.

Further, in the field of semiconductor integrated circuits in particular, a dielectric isolation technique adapted to isolate individual elements by means of dielectrics is excellent in respect the the parasitic capacity and isolation characteristics, but undesirably makes the substrate excessively large in warp. For this reason, the dielectric isolation technique involves a great disadvantage from a manufacturing standpoint.

Further, almost no attention has hitherto been paid to a method of bonding together the polished mirror surfaces, either directly or with an oxide film interposed therebetween, of two silicon wafers. However, much attention has lately been paid to a method of manufacturing a substrate for the above-mentioned high power device, or a substrate for the above-mentioned dielectric isolation. That is to say, in any application, the silicon wafer mirror surface bonding method can remarkably solve the above-mentioned drawbacks of the prior art.

The existing silicon wafer bonding method includes a method of merely superposing one silicon wafer mirror surface upon the other at room temperature in an ordinary air atmosphere, and heating the superposed wafer body at high temperature, for example, of 1,100° C. for about two hours in a specially mixed atmosphere of oxygen and nitrogen gases bearing the ratio of 1:5 and a method of, in the case where an oxide film exists in between the method involves, applying a direct current or alternating current voltage across the wafers at the time of superposing them one upon the other so as to utilize electrostatic force acting between the wafers and then heating the superposed wafers in an atmosphere of nitrogen gas.

The technical problem concerning the mutual bonding of two silicon wafers resides in the respect that some unbonded regions are left between the opposing surfaces of the two mirror surface wafers, as a result of insufficient proximity, and that in consequence what is usually called "voids" are formed. In order to prevent the formation of such voids, studies have been made on the causes of formation of them. The causes can be considered to be dust particles or contaminations, or scratches having attached onto, or having been caused to the surfaces of the wafers. In particular, attention is drawn toward dust particles as the greatest cause of creating such voids.

The present inventor, however, has experimentally confirmed that it is impossible to completely prevent the formation of voids even by removal of all of the above-mentioned causes.

Further, as an improved silicon wafer bonding technique, Japanese Patent Unexamined Publication No. 61-182216, for instance, proposes a method wherein a gas which is easy to pass through or to be absorbed by the semiconductors is used as an atmosphere at the time of bonding wafers together to prevent such voids. Once a gas has been held in the interface between the bonded surfaces of silicon wafers, however, removal of such gas by penetration and absorption thereof is very difficult in actuality.

As another void preventing method, Japanese Patent Unexamined Publication No. 63-93107, for example, proposes a method of activating the bonded surfaces by irradiation of microwaves. This method, however, has a drawback in that it requires the use of a special system for irradiation of microwaves.

If the bonded surfaces of the wafers form a boundary or interface of an active region of a device, it is a problem whether a complete epitaxy is formed or not at the bonded interface. In a general bonded interface utilizing method, however, the bonded surfaces are indeed made to come close to the active region but consideration is given so that they may not come into the same. Accordingly, making the bonded interface completely monolithic is ordinarily not required.

However, there is a likelihood that, in case the bonded surfaces come close to the active region, the defective bonded interface sometimes causes the active region to have a crystalline disorder or a physical imperfection. Further, there is also a likelihood that the defective bonded interface causes performance characteristics of a power transistor, for instance, to be deteriorated. To eliminate such a likelihood, it is desireable to substantially eliminate the unbonded regions in the bonded interface and to provide a void-inspection method which is effective in substantially eliminating them.

In general, inspection of the bonding condition is conducted by utilizing an infrared transmission image. In this method, infrared rays are irradiated onto the bonded wafers from a direction perpendicular to the interface of the bonded wafers, to thereby facilitate observation a transmission image as obtained. Unbonded regions are observed as white image portions while bonded regions are observed as black image regions. When infrared radiation has been incident upon the bonded surfaces of wafers substantially at right angles thereto, if there exists any unbonded region in the bonded interface, reflection, absorption and a change in refractive index take place at such an unbonded region. For this reason, the transmitted amount of light is reduced as compared with that which is obtained from the bonded regions. The lightness and darkness of a transmission image are reversed one to the other depending upon the method of observation.

However, it has been experimentally proved that this method fails to detect any unbonded regions unless the gap between the bonded surfaces at the unbonded region is considerably large in dimension, for example, 0.1 μm or more.

The unbonded regions each of which has a gap or clearance of a below 0.1 μm can be observed only by suitably cutting the bonded wafers and observing the cut surface thereof with use of SEM (Scanning Electron Microscope). This method of observation, however, is a destructive inspection and, in addition, fails to observe the unbonded regions which are not included in such a cut surface.

For the above-mentioned reasons, there has eagerly been desired the development of an easy and nondestructive inspecting method of bonded wafers to determine whether the bonded interface is perfectly bonded or not.

SUMMARY OF THE INVENTION

The present invention has been made in view of the above-described prior art problems, and an object thereof is to provide a method of inspecting bonded wafers without destruction and which easily determines whether or not the bonded surfaces of the bonded wafers are in a condition of being substantially bonded together.

To attain the above object, according to the present invention, there is provided a method of inspecting bonded wafers which comprises the steps of taking a X-ray Lang topograph of bonded wafers, treating an image thereon, and detecting unbonded regions at the interface of the bonded wafers. The bonded wafers are constituted by, for example, silicon wafers or compound semiconductor wafers.

In bonding two silicon wafers to each other, an oneside surface of each silicon wafer is finished into a mirror surface and then is cleaned to a sufficient extent. Subsequently, both the mirror surfaces of the two silicon wafers are just superposed one upon the other and lightly pressed to each other, and then the superimposed wafers are subjected to a high-temperature heat treatment. Unless, in this initial stage, the opposing surfaces completely contacted each other, the degree of bonding would hardly be enhanced any more even by the subsequent high-temperature heat treatment. The high-temperature heat treatment is conducted mainly for the purpose of removing distortions on the bonded surfaces, making the bonding interface integral or monolithic, and absorbing and diffusing a very small amount of atmospheric gas.

Theoretically speaking, if the respective, and mutually opposing, surfaces of both wafers are completely flat on an atomic level and yet are free from any contamination, making a monolithic structure from both wafers is effected by the inherent bonding force between the atoms of one wafer surface and those of the other only by contacting the two wafers to each other.

Under the actual industrial manufacturing circumstances, however, both the wafer surfaces are fairly far from such an ideal condition. Accordingly, it is of great significance to find out the requirement of making bonding wafers, which are good enough to manufacture a complete electronic device, using an industrially possible working process, etc. as widely and sufficiently as possible.

A wafer surface to be bonded has a considerable level of microscopic roughness. At the respective convexities on the surface of bonded wafers, therefore, the crystal is subjected to a rather large amount of distortion at its bonding interface. In this case, each surface can be classified into two regions. In one region (composed of bonded regions), the distances between the bonded surfaces are in coincidence with the lattice distance. In the other region (composed of unbonded regions), the distances are larger than the lattice distance. The bonding strength at the bonded regions is attributable to the bonding force between silicon atoms of one wafer surface and those of the other, and one atmospheric pressure is added thereto. By way of heat treatment conducted after the wafers have been contacted, the wafer surface distortions are released or corrected with the result that the silicon atoms can be moved so as to fill up the small gaps where both the wafer surfaces are slightly spaced apart from each other. However, such movements of the silicon atoms are considered not to greatly enhance the degree of bonding between the two wafers.

In the present invention, bonded wafers are disposed as a sample in a Lang camera. The angle of divergence of X-ray flux generated from an X-ray source is limited by a first slit. At the back of the sample (bonded wafers), there is disposed a second slit whose width is wider than that of the first slit so as to permit the passage therethrough of, for example, only a diffracted X-rays of MoKα, thereby causing only the diffracted X-rays to reach, for example, a photographic plate. Under the conditions in which diffracted X-rays are passed in the above-mentioned way, a scanning table on which the crystal unit and the photographic plate are placed is reciprocatingly moved in parallel with the surface of the crystal unit to obtain a diffraction image (Lang topograph) of a wide area of the wafers.

At this time, the crystal orientations of the silicon wafers desirably are in perfect coincidence with each other at the bonding interface between the two wafers. Desirably, where wafers are superposed one upon the other, the crystal surfaces are within a range of $-2°$ to $+2°$ in terms of the surface orientation. More specifically, if the orientation of the principal wafer surface is set at (100) $\pm 1°$ and the orientation of the orientation flat surface is set at (110) $\pm 1°$, it would result that the crystal orientations of the two wafers at the bonding interface sufficiently coincide with each other when the two wafers are superposed one upon the other with the orientation flat surface being in coincidence with each other.

In the Lang topograph, a contrast would be produced between the regions having some distortion and the regions having no distortion due to extinction effects attributable to the fact that X-rays are spherical waves. In the bonded wafers, a bonded region will surely have some distortion at the interface between the bonded wafers, while an unbonded region will have no distortion. Accordingly, it is possible to detect the unbonded regions with high sensitivity by preparing a Lang topograph and detecting any distortion occurring at the interface.

In the infrared ray transmission system as conventionally employed, an unbonded region can not be confirmed as an unbonded region unless the gap between the unbonded surfaces is 0.1 μm or more. In contrast, the present invention enables the detection of whether or not the bonded surfaces are substantially bonded together. Therefore, it can be said that the present invention provides a bonded wafer inspecting method which is excellent in substance as compared with the prior art method. This fact has been confirmed by bonding together wafers each having a surface roughness of about 1 nm and comparing the bonded condition as detected by the infrared ray transmission method with the bonded condition as detected by the method of the present invention. Namely, in the former method, a completely bonded state image was obtained while, in the latter method, a plurality of dotted unbonded regions could be confirmed to exist in the image.

The wafers which were confirmed, by the method of the invention, to have been completely bonded together were diced to 0.5 mm$^2$ in order to inspect unbonded regions. As a result, any chip did not separate and it was confirmed that the wafers had been completely bonded and had not been detected for any visible gap between them, although the boundary was slightly observed when the bonding interface was observed by microscope.

It is said that the use of X-rays makes it possible to detect a change in lattice constant d down to $\Delta d/d \approx 10^{-7}$ when $\Delta d$ is assumed to represent an amount of change in lattice constant d. This is considered to be a reason why, in accordance with the method of the invention, a slight change in lattice constant at the interface of the bonded surfaces, i.e., unbonded regions of the bonded wafers, can be detected with high sensitivity. In other words, unbonded regions can be detected with high sensitivity by this method.

The reason why unbonded regions defining small gaps therebetween can not be detected in accordance with the infrared ray transmission method is considered as follows. When the gaps at the unbonded surface regions become sufficiently small, reflection, refraction and absorption of infrared rays in the gaps and at the interface regions thereof can not be discriminated from those in case of bonded interface regions. For this reason, no effect is had upon the intensity of the transmitted light.

Although the foregoing description has referred to the case where silicon wafers are directly bonded together, the same explanation as made above applies also to the case where an oxide film or films are interposed between such silicon wafers. Since, in this case, an oxide film is formed on the silicon wafer, when the oxide film becomes thick, distortion is created in the crystalline layer due to the difference in thermal expansion coefficient between the oxide film and silicon. As a result, the image of the Lang topograph becomes slighly unclear but this method can sufficiently serve the purpose.

Further, since the present invention makes use of X-ray radiation, it can be applicable when the wafers employed are single crystals and can also be sufficiently practically applied to compound semiconductors as well.

DESCRIPTION OF THE PREFERRED EMBODIMENTS (1) Embodiment

An embodiment of the present invention will now be described with reference to the drawings.

Figure 1:
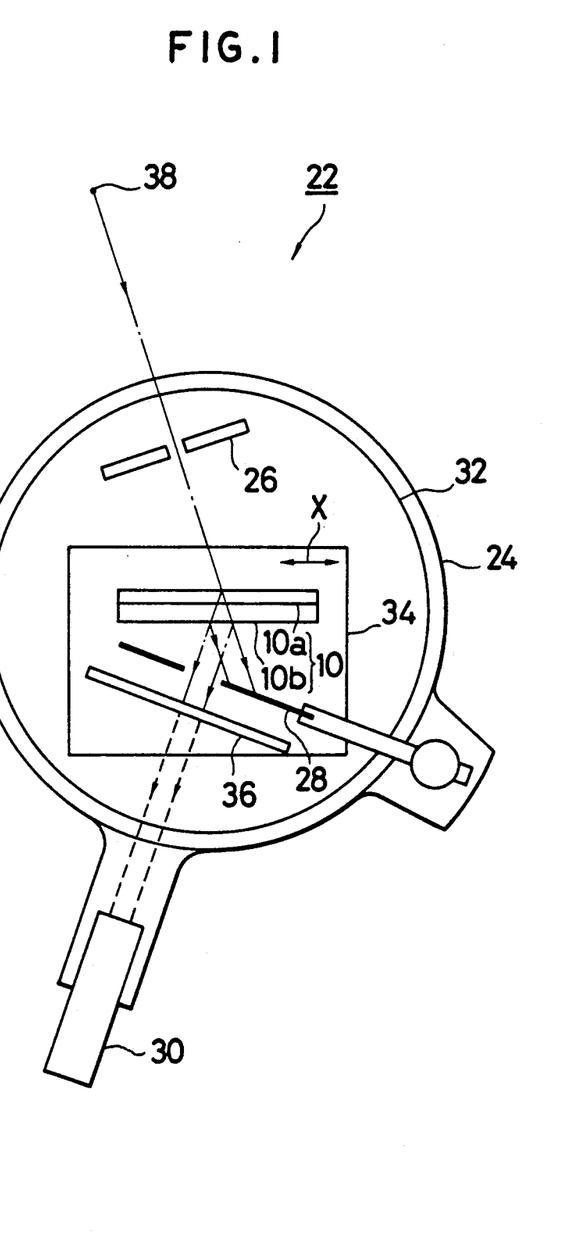
FIG. 1 is a schematic constructional view showing an example of a Lang camera.
Figure 2:
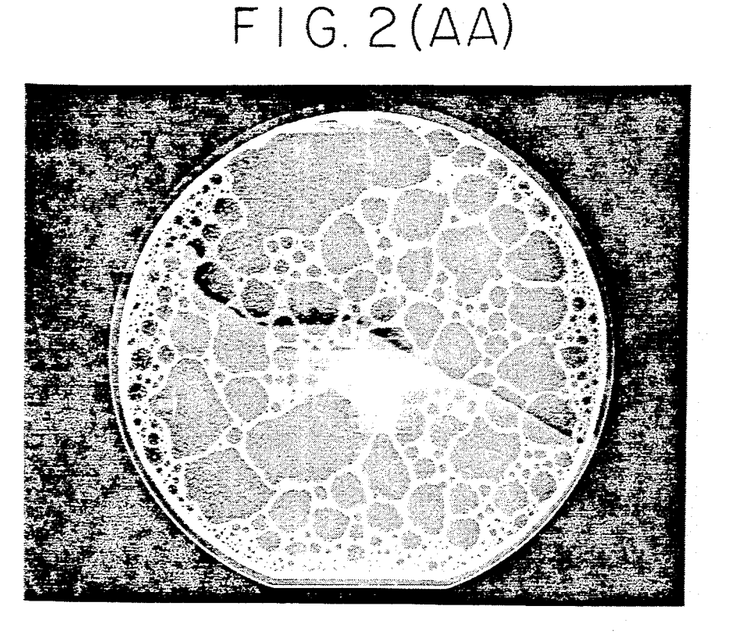
FIGS. 2 to 11 are X-ray photographs of bonded wafers prepared by use of a Lang camera.
Figure 3:
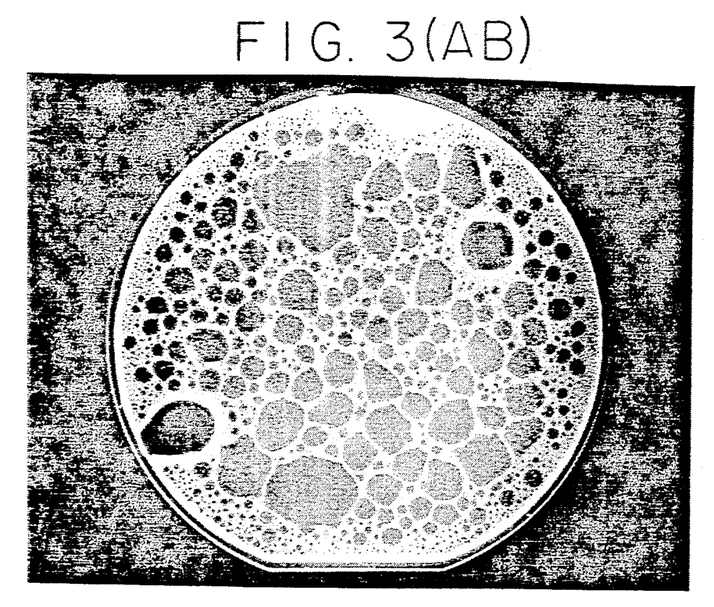
Figure 4:
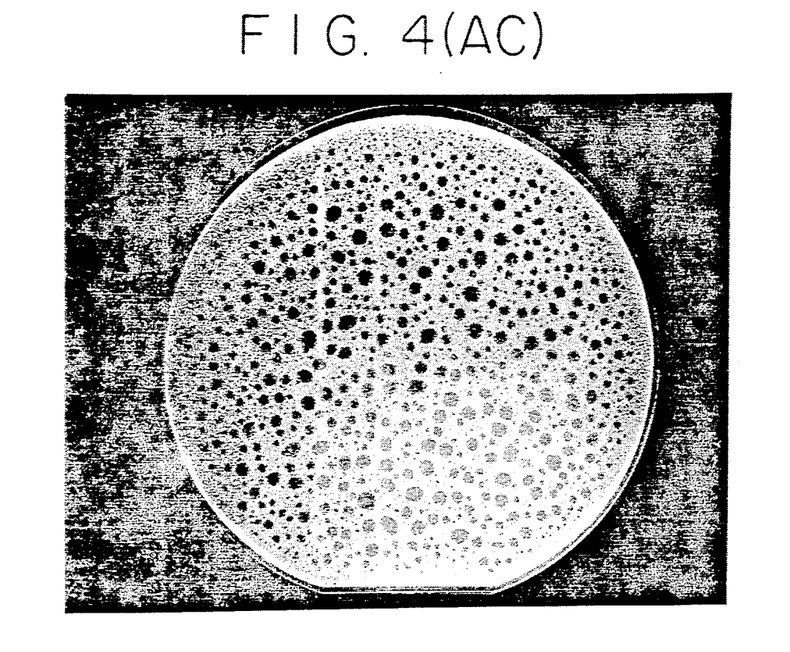
Figure 5:
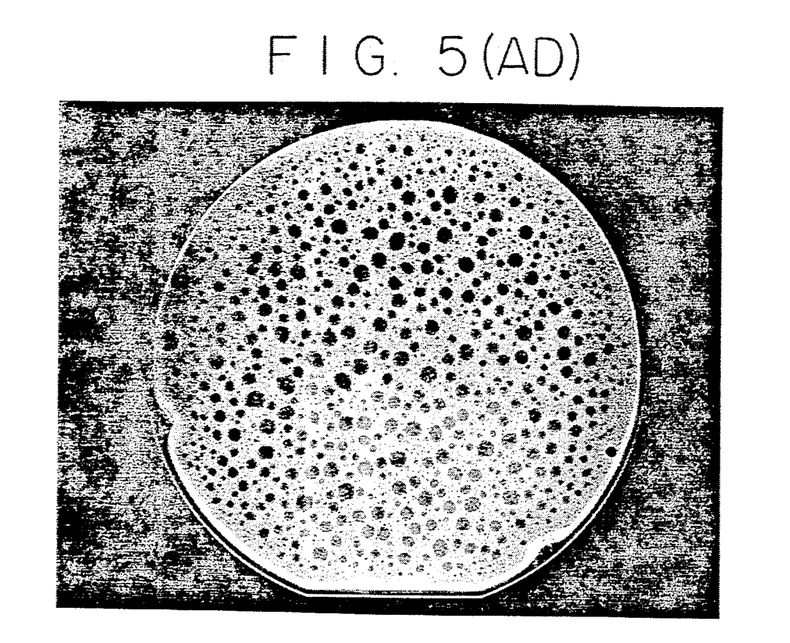
Figure 6:
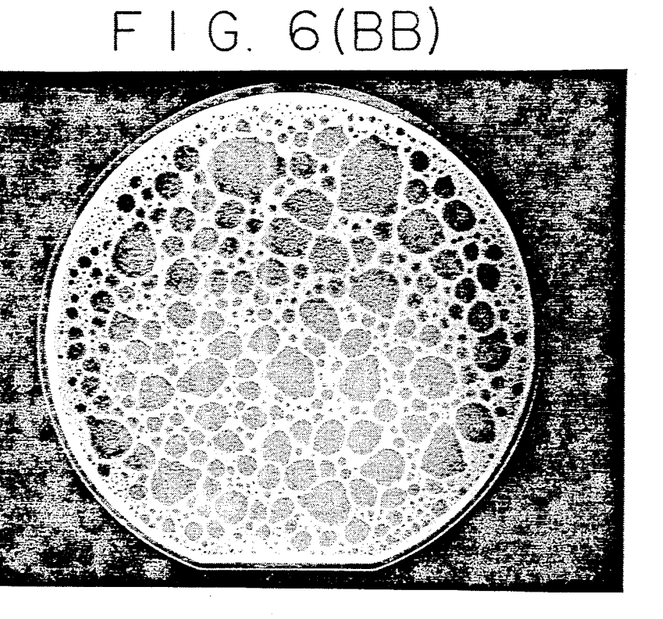
Figure 7:
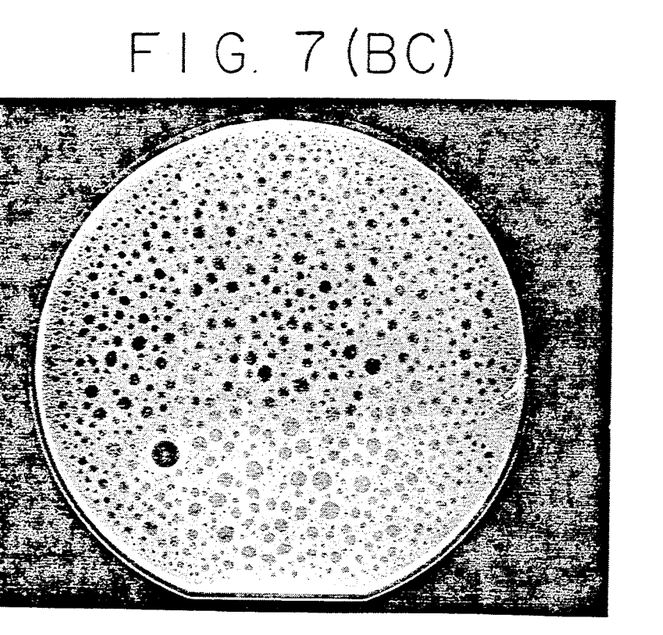
Figure 8:
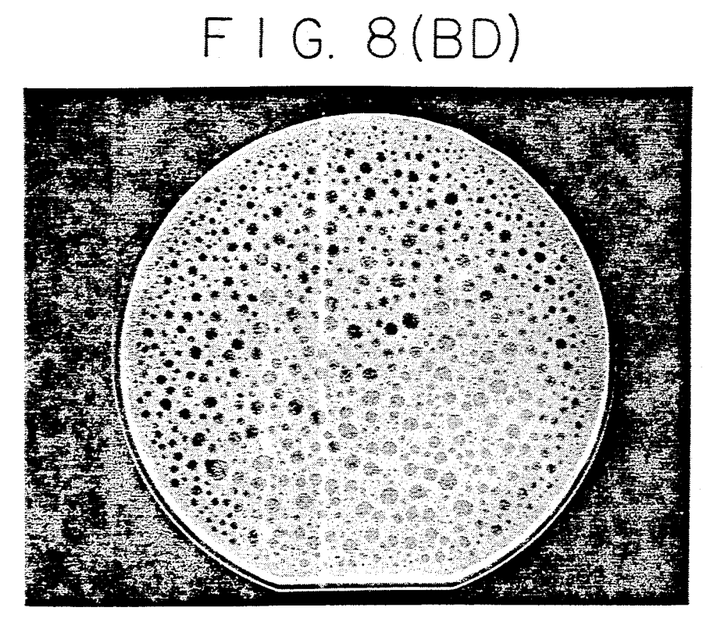
Figure 9:
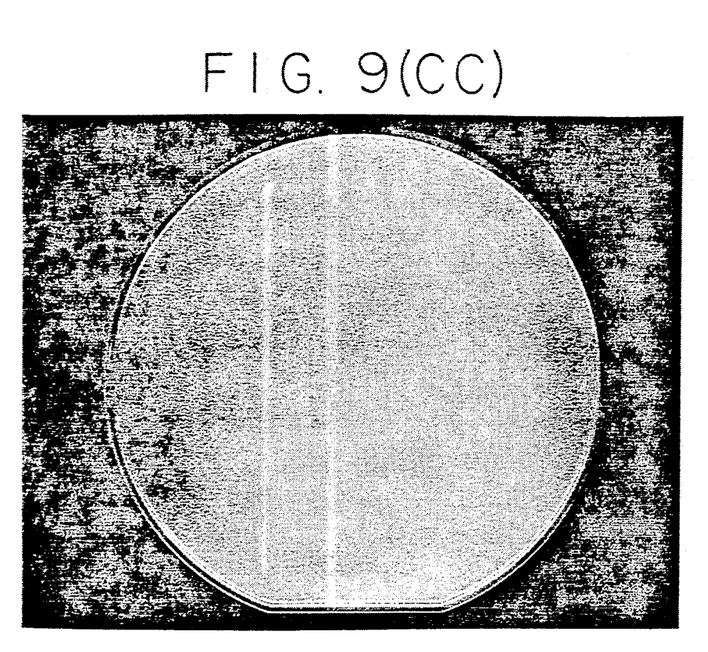
Figure 10:
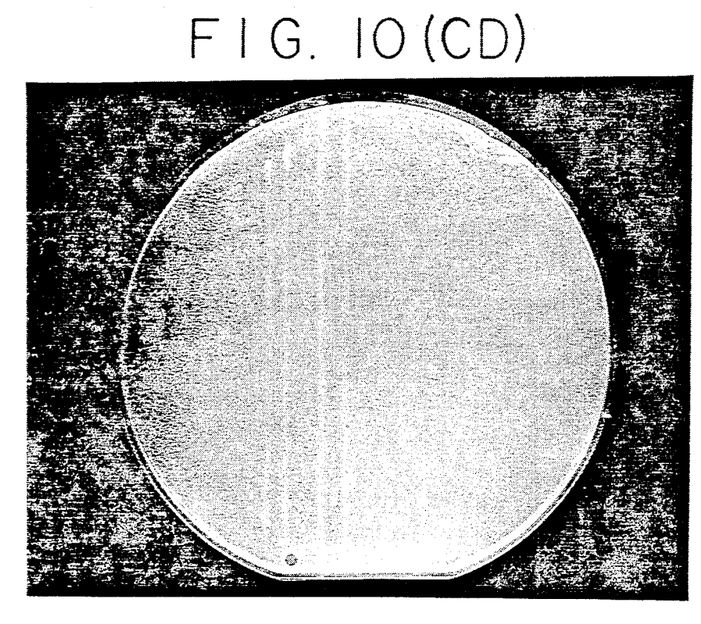
Figure 11:
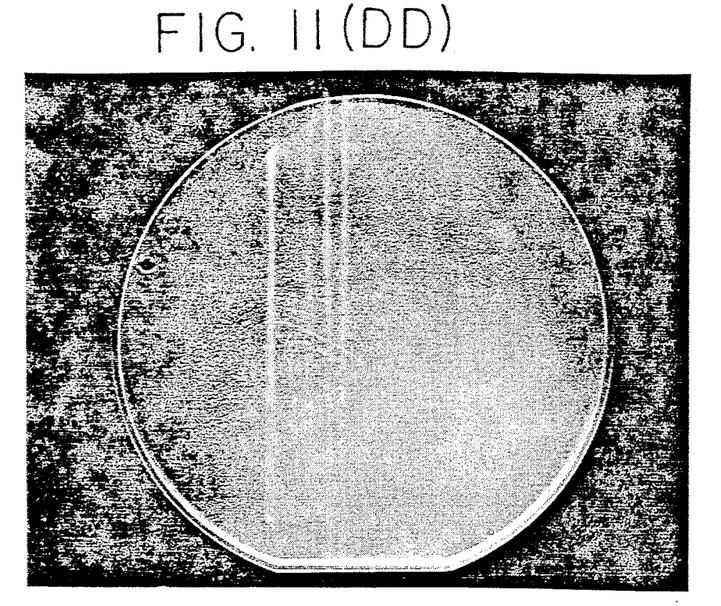

FIG. 1 shows a state wherein bonded wafers 10 composed of wafers 10a and 10b are disposed as a sample in a Lang camera 22 known to those skilled in the art.

The Lang camera 22 has a $2\theta$ rotary table 24 on which a first slit 26, a second slit 28 and a counter 30 are fixed. A $\theta$ rotary table 32 is rotatably supported relative to the $2\theta$ rotary table 24. The table 32 is mounted thereon with parallel displacement scanning table 34 in such a manner that the table 34 is permitted to freely conduct the scanning operation in an X direction. On this parallel displacement scanning table 34 there are vertically fixed bonded wafers 10 and a photographic plate 36.

Adjustment of the Lang camera 22 is conducted in the following manner. That is to say, the $2\theta$ rotary table 24 is rotated, whereby the counter 30 is fixed in a direction which permits the diffracted X-rays from the bonded wafers 10 to go into the counter 30. Then, the $\theta$ rotary table 32 is so rotated as to permit only the $K\alpha|$ rays to be diffracted. The degree of opening of the second slit 28 is made high in advance. Next, an X-ray flux from an X-ray source 38 is passed through the first slit 26. Thereafter, the degree of opening of the second slit 28 is so adjusted that only the diffracted X-rays may reach the photographic plate 36 while viewing the output display of the counter 30.

Next, the photographic plate 36 is fixed on the parallel displacement scanning table 34. Thus, a Lang topograph, or a diffraction image, of a wide area of the bonded wafers 10 are obtained through reciprocating movements of the parallel displacement scanning table 34 in the X directions (the directions parallel to the surface of the bonded wafers 10). (2) Example of Inspection of the Bonding Condition An example of inspection of the bonding condition will now be described. Single crystal silicon wafers A to D having surface roughnesses shown in Table 1 below were used as samples.

TABLE 1

| Wafer | Center Line Average Roughness |
|---|---|
| A | 0.73 |
| B | 0.57 |
| C | 0.45 |
| D | 0.37 |

Numerical values in Table 1 above are ones as measured in unit of nm. The surface roughnesses in Table 1 above were measured using a non-contact micro-surface measurement system TOPO—3D as manufactured by WYKO CORPORATION, the system being equipped with an objective lens having a magnification 40.

In order to clarify the relation between the surface roughness and the formation of voids, each of the above wafers A to D was prepared four in number, mirror surfaces of all combined wafers (AA, AB, AC, AD, BB, BC, BD, CC, CD, and DD) were superposed to each other, and superimposed. Then the resulting wafer units were heat-treated at 1,100° C. for 120 minutes in an atmosphere of N$_2$. Thus, a group of bonded wafers were produced.

The bonding conditions were inspected using a Computer-Controlled Topograph Imaging System as manufactured by RIGAKU CORPORATION. The characteristic X-rays used were MoK$\alpha$ rays and the reflecting lattice plane as set had a Miller indices of (2, 2, 0).

FIGS. 2 to 11 show the X-ray topographs of the group of above-bonded wafers AA to DD which have been prepared by using a Lang camera.

When attention is drawn toward the dark spots alone attributable to the surface roughness, it is clear that the total area of all dark spots of each bonded wafers is decreased in the order of AA>AB>BB>AC->AD>BC>BD >CC>CD>DD. It is also clear that some of the bonded wafers CC, CD and DD have almost no dark spot and therefore the corresponding wafer bonding conditions are very good as compared with the wafer bonding condition of the other combined wafer units.

Whether or not the dark spots were voids was made by use of SEM (Scanning Electron Microscope) based on destructive inspection.

It will be understood from the above experimental results that where bonding of wafers is effected without forming any oxide film on the mirror surfaces, setting the mirror surface roughness to a center line average roughness of 0.45 nm or less is very important for preventing the formation of voids. This fact has been made clear by application of the method in accordance with the present invention. Accordingly, the present invention is of great significance.

(3) Other embodiments

It is to be noted that the invention permits other changes or modifications thereof to be made without departing from the subject matter of the invention.

For example, although the foregoing embodiment has referred to the case where a photographic plate 36 is disposed in a Lang camera, a highly sensitive TV camera may be disposed via a fluorescent screen in the same position as that at which the photographic plate 36 is disposed, and the image can be displayed on a monitor television. By so doing, in the process of producing bonded wafers, it is possible to conduct the void inspection on an on-line basis. This system becomes operable only when it is used in combination with an X-ray source of ultrahigh intensity.

As has been described above, according to the void inspection method of the present invention, a Lang topograph of bonded wafers as a sample is prepared and the resulting image is treated so as to detect unbonded regions at the interface of the bonded wafers. Therefore, it is possible to substantially detect any unbonded regions. Thus, the invention can greatly contribute to enhancing the bonding quality of bonded wafers.

What is claimed is:

1. A method of inspecting bonded wafers to determine whether the wafers have been completely bonded together, comprising the steps of:

placing a bonded wafer for inspection into a Lang camera;

activating an X-ray energy source of high intensity to impinge on the bonded wafer;

adjusting the position of the bonded wafer along one direction while the energy source is impinging thereon; and obtained a Lang topograph of the bonded wafer.

2. A method as in claim 1 comprising the further step of displaying the obtained Lang topograph.

3. A method as in claim 2 wherein said displaying step comprises displaying the obtained Lang topograph on a television monitor.

* * * * *